United States Patent [19]

Schäfer et al.

[11] Patent Number: 4,900,932
[45] Date of Patent: Feb. 13, 1990

[54] CATHODOLUMINESCENCE DETECTOR UTILIZING A HOLLOW TUBE FOR DIRECTING LIGHT RADIATION FROM THE SAMPLE TO THE DETECTOR

[75] Inventors: Norbert Schäfer; Eugen Weimer; Herbert Gross, all of Essingen; Bernd Eppli, Königsbronn; Eberhard Rossow, Oberkochen, all of Fed. Rep. of Germany

[73] Assignee: Carl-Zeiss-Stiftung, Heidenheim/Brenz, Fed. Rep. of Germany

[21] Appl. No.: 239,317

[22] Filed: Sep. 1, 1988

[30] Foreign Application Priority Data

Sep. 5, 1987 [DE] Fed. Rep. of Germany ....... 3729846

[51] Int. Cl.⁴ .......................................... H01J 37/244
[52] U.S. Cl. ................................. 250/397; 250/310; 250/306; 250/216; 356/225
[58] Field of Search ............... 250/397, 310, 306, 216; 356/318, 446, 440, 218, 225, 236

[56] References Cited

U.S. PATENT DOCUMENTS

| | | | |
|---|---|---|---|
| 3,790,781 | 1/1974 | Horl et al. | 250/310 |
| 4,463,257 | 7/1984 | Simpkins et al. | 250/310 |
| 4,597,665 | 7/1986 | Galbraith et al. | 356/237 |

FOREIGN PATENT DOCUMENTS

| | | | |
|---|---|---|---|
| 207994 | 3/1984 | German Democratic Rep. | |
| 54-18269 | 2/1979 | Japan | 250/310 |
| 2079486 | 1/1982 | United Kingdom | 356/311 |

OTHER PUBLICATIONS

Article, "Verbessertes Ellipsenspiegel-Detektorsystem für die Kathodolumineszenz-Rasterelektronenmikroskopie" by E. M. Hörl in Beiträge electronenmikroskopischer Direktabbildungen von Oberflächen, 8, p. 369, (1975).

Primary Examiner—Jack I. Berman
Attorney, Agent, or Firm—Walter Ottesen

[57] ABSTRACT

A detector is disclosed which includes an elliptical hollow mirror and a tube having a reflecting inner surface for conducting the light emitted by a specimen under investigation in a scanning electron microscope. A vacuum window is seated at the outer end portion of the tube directly ahead of a receiver.

24 Claims, 2 Drawing Sheets

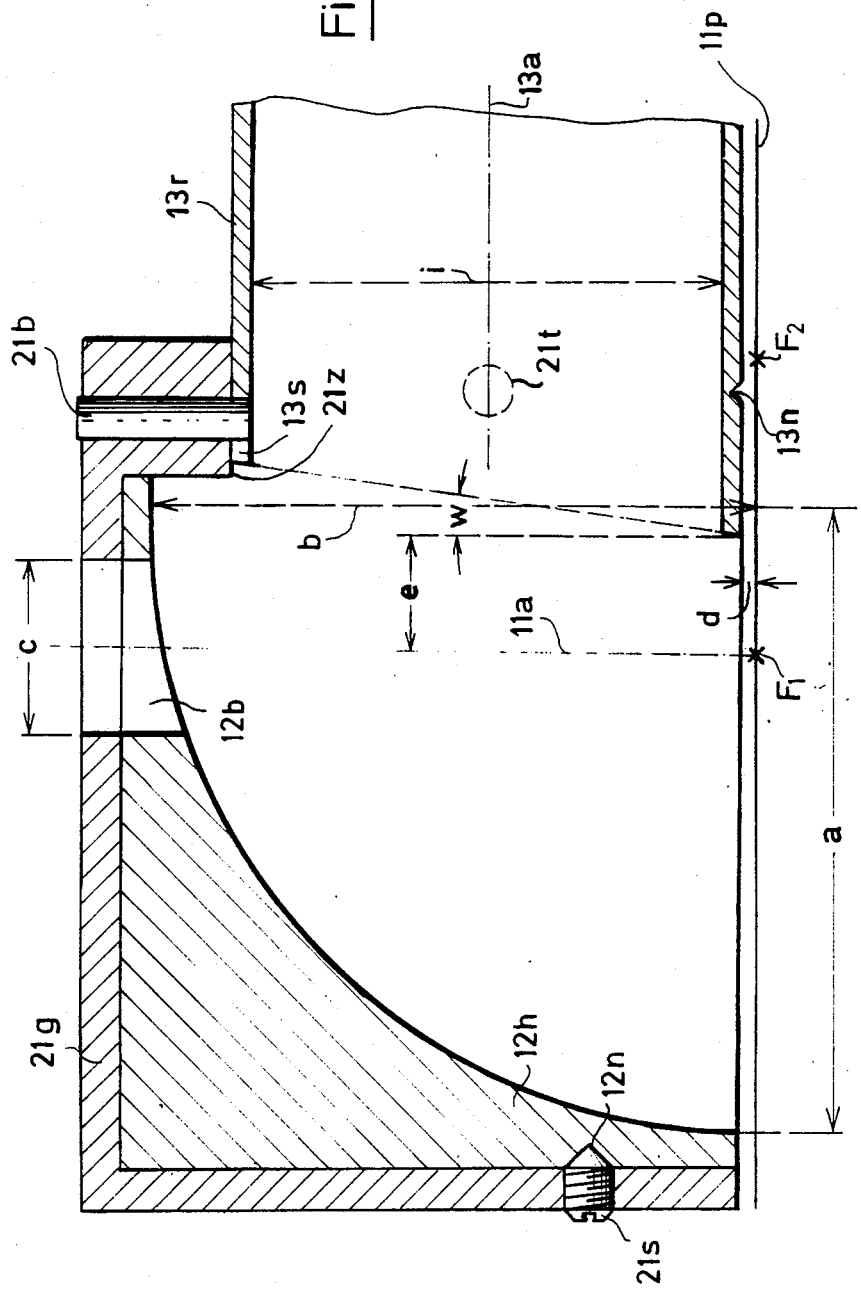

CATHODOLUMINESCENCE DETECTOR UTILIZING A HOLLOW TUBE FOR DIRECTING LIGHT RADIATION FROM THE SAMPLE TO THE DETECTOR

FIELD OF THE INVENTION

The invention relates to a cathodoluminescence detector having a spherical or aspherical concave mirror and a vacuum window made of glass or plastic. The detector also includes a photoelectric receiver. Detectors of this type are preferably utilized in scanning electron microscopes (SEM).

BACKGROUND OF THE INVENTION

In an electron microscope, the specimen to be investigated is scanned in a meander-like manner with an electron beam focused on the specimen. This leads to various interactions on the specimen. Cathodoluminescence is understood to be the emission of quantums of light in the visible or neighboring spectral ranges by the electron beam. Images are generated, for example, on a monitor, with the aid of suitable detectors and an image buildup corresponding to the scanning movement of the electron beam. These images correspond to the light emission of the specimen. In this connection, specific spectral regions can be separated out, for example, by means of a filter. Often, also other interactions between the electron beam and the specimen are simultaneously investigated with additional detectors, for example, secondary electrons.

East German Patent 207,994 discloses a cathodoluminescence detector wherein a paraboloid mirror is mounted between the pole shoe of the last electron optical lens and the specimen. The parabolic mirror has a bore for the electron beam and reflects the light emanating from the specimen lying in its focal point as a parallel light handle onto a lens which concentrates the light bundle onto a photoelectric receiver. A disadvantage of this arrangement is that the paraboloid has to be relatively large for a good exploitation of the light and therefore the specimen must be inclined toward the electron beam. As a consequence of the foregoing, the dimensions of the specimen are limited.

Reference may also be made to an article entitled "Verbessertes Ellipsenspiegel-Detektorsystem für die Kathodolumineszenz-Rasterelektronenmikroskopie" by E. M. Hörl appearing in the journal entitled "Beiträge elektronenmikroskopischer Direktabbildungen von Oberflächen 8, page 369 (1975). This publication discloses a cathodoluminescence detector wherein the specimen is mounted in the one focal point of an elliptical mirror and wherein a parabolic mirror is additionally mounted for the best possible light exploitation such that its focal point lies in the second focal point of the ellipse. Although the specimen here must not be inclined with respect to the electron beam, its magnitude is, however, likewise limited by the parabolic mirror. This publication also discloses the use of a light conductor as a vacuum window.

SUMMARY OF THE INVENTION

It is an object of the invention to provide a cathodoluminescence detector which provides a good exploitation of light and nonetheless does not limit the size of the specimen. Furthermore, the cathodoluminescence detector should be utilized simultaneously with other detectors and be easily removed from the beam path.

The above object is achieved with a cathodoluminescence detector according to the invention by means of a concave mirror in that this mirror is attached to a tube having an inner surface which is configured so as to be reflective. Pursuant to another feature of the invention, the vacuum window is mounted in this tube or at the end thereof facing toward the receiver.

In an advantageous embodiment of the invention, the vacuum window is made of a cylindrical glass or plastic part which is at least partially mounted in the reflecting tube. The vacuum window is connected with the tube in a vacuum-tight manner by means of a sealing ring pressed in the direction of the tube axis.

It is especially advantageous to mount the vacuum window at the outer end of the tube such that the window of the receiver lies directly therebehind. In this way, not only are reflection losses via an intermediate air space between the vacuum window and the window of the receiver prevented; but also, the vacuum window is mounted as far as possible from the specimen so that the generation of luminescent light in the specimen by means of backscattered electrons is very low.

If the tube were replaced with a cylindrically-shaped light conducting rod which could at the same time be configured as a vacuum window, then with specimens having reduced cathodoluminescence, their luminescent radiation would be superimposed too intensely by the luminescent radiation generated by backscattered electrons in the light conductor rod.

In a further advantageous embodiment of the invention, the concave mirror is seated in a fitting which is insertable on the reflecting tube in a reproducible manner. In this way, measurements without the concave mirror also can be carried out with the detector which is possible with specimens having an intense cathodoluminescence. This has the advantage that more space remains for further detectors.

In an especially advantageous embodiment of the invention, the reflecting tube with the receiver is displaceable in the direction of the tube axis and is journalled in a vacuum-tight manner in the wall of the specimen chamber. In addition, means are present which effect a reproducible positioning of the inner end of the tube in the inserted condition. If required, and together with the reproducible seatable fitting of the concave mirror, the possibility is provided of investigating a specimen in time sequence with various detectors one after the other.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
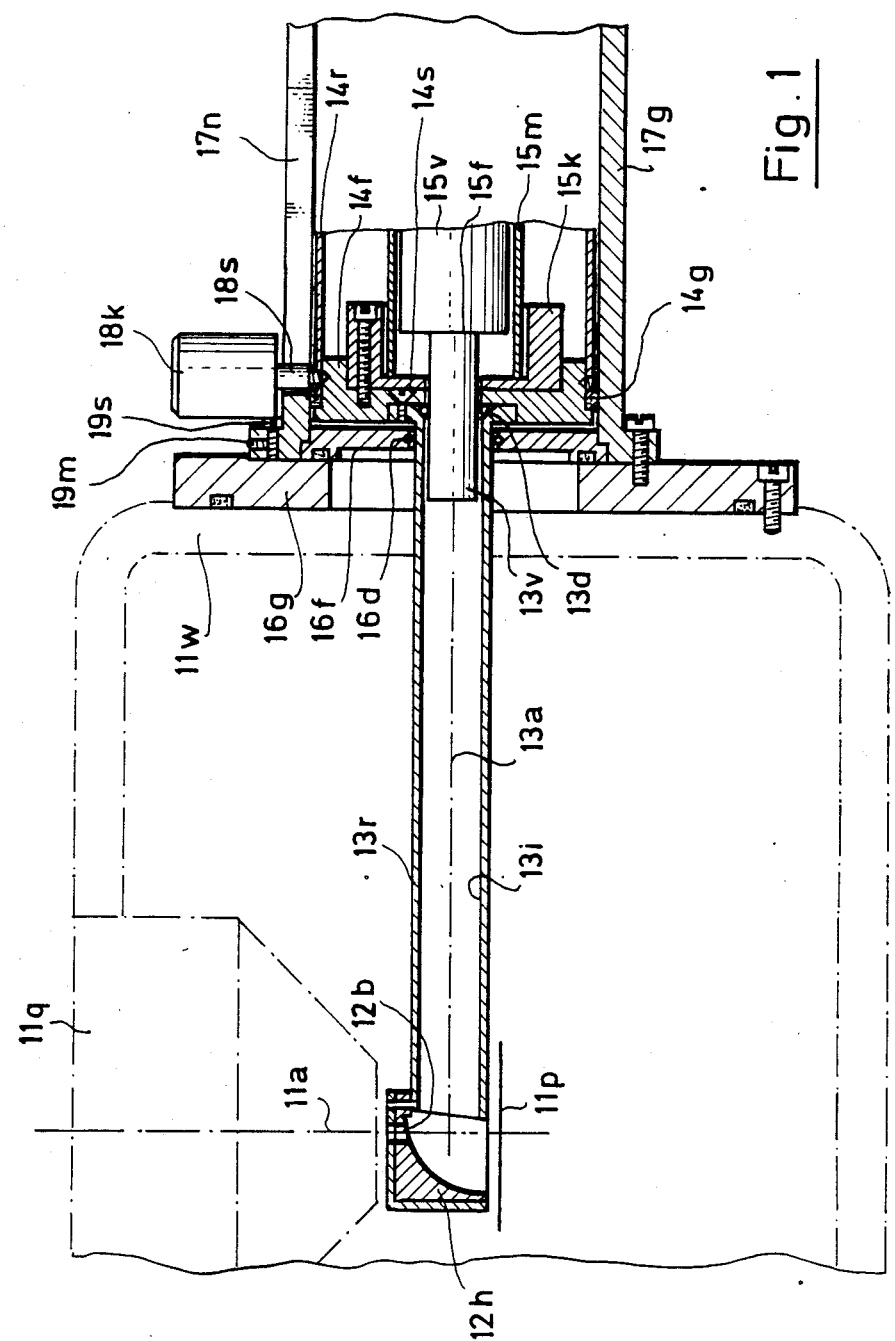
FIG. 1 is a section view taken through a detector according to an embodiment of the invention; and, FIG. 2 is a section view in an enlarged scale taken through the hollow mirror and its fitting and the front end of the tube on which the latter are mounted.

In FIG. 1, a specimen is identified by 11p and the last electro-optical lens is identified with reference character 11q. The center axis of the electron beam is identified by 11a and 11w identifies the wall of the specimen chamber of a scanning electron microscope. The concave mirror 12h is disposed between the specimen 11p and the electro-optical lens 11q and includes a bore 12b for the electron beam which impinges upon the specimen 11p and scans the latter in a meander-like manner. The concave mirror 12h collects the light emitted by the specimen as described in more detail below with respect to FIG. 2. The concave mirror 12h is connected to the tube 13r which passes through the wall 11w of the specimen chamber and can be, for example, a spherical concave mirror.

The tube 13r is preferably made of aluminum and the inner wall surface 13i thereof is polished so well that it conducts the light collected from the concave mirror 12h and reflected into the tube as well as the light emitted directly into the tube until the same enters the vacuum window 13v. The vacuum window 13v is made of glass or plastic and has the form of a cylinder. The vacuum window 13v is connected to the tube 13r via the sealing ring 13d. This sealing ring 13d is seated on a conical surface at the end of the tube 13r. The sealing ring 13d is pressed in the direction of the tube axis 13a by means of the flange 14f and the screws 14s such that a vacuum-tight connection is established between the cylindrically-shaped vacuum window 13v and the tube 13r.

Within the vacuum window 13v, the light impinges upon the cylindrically-shaped outer surface substantially at an angle which is greater than the critical angle of the total reflection so that no reflective coating of this outer surface is required. The window 15f of the multiplier 15v is pressed directly against the end of the vacuum window 13v by means of a resilient holder (not shown) of the multiplier socket so that only small reflection losses occur at the crossover as a consequence of the good flatness of the participating surfaces.

It is understood that the multiplier can be replaced by another suitable receiver. Likewise, it is also possible to mount a filter or a monochromator between the vacuum window 13v and the multiplier 15v to mask out specific spectral regions. Finally, the receiver can be replaced by a diode-array spectrometer with the connection thereof via a flexible light conductor being especially advantageous with the light conductor being placed directly on the vacuum window.

The tube 13r is connected with the flange 16f in a vacuum-tight manner by means of seal 16d and is displaceable in the seal 16d in the direction of its axis 13a. This displacement is furthermore guided and limited by means of the housing 17g in which the tube 14r is displaceably mounted. The tube 14r is connected with tube 13r via flange 14f. The exact guidance of the tube 14r in the housing 17g is provided by a slide ring 14g. The displacement of the concave mirror 12h in and out of the beam path is achieved with the handle 18k having a pin 18s which passes through the slot 17n of the housing 17g and threadably engages the flange 14f. At the same time, rotational movements of the tube 13r about its axis 13a are prevented by means of the pin 18s in the slot 17n. The end position of the detector inserted into the beam path is adjusted with the screw 19s on the housing 17g and this end position of the detector is fixed with the stud screw 19m. In addition, a plastic part 15k and the mu-metal shielding cup 15m for the multiplier 15v are seated in the flange 14f.

The entire arrangement is mounted on flange 16g which is removably mounted on a corresponding opening in the wall 11w of the specimen chamber. The flange 16g can be provided with further known adjusting arrangements.

In FIG. 2, the head of the detector is shown at an increased scale. The concave mirror 12h is seated in a housing 21g and is held therein by means of screws 21s which engage in slots 12n of the concave mirror. The housing 21g has a bore 21z which includes almost an entire cylindrical periphery and with which it is seated onto the tube 13r. In this connection, a bolt 21b in the housing 21g engages the slit 13s milled into the tube 13r and in this way brings the housing 21g into a reproducible position with respect to the tube 13r. The housing 21g is furthermore fixed by means of screws 21t which engage in a slot 13n in the tube 13r.

FIG. 2 shows the particular distances and angle for which the following values provide an advantageous dimensioning example:

a = 18.5 mm
b = 18.0 mm
c = 5 mm
d = 0.5 mm
e = 3.5 mm
i = 14 mm
w = 12°

The hollow mirror 12h is a rotational ellipsoid having focal points F1 and F2 lying on the surface of specimen 11p. The diameter c of the bore 12b can be reduced for high magnifications whereby the efficiency of the detector is improved. Furthermore, the axis 13a of the tube 13r can define a small angle with respect to the large semiaxis (a) of the rotational ellipsoid so that only the forward part with the concave mirror 12h must come as close as necessary to the specimen 11p.

It is understood that the foregoing description is that of the preferred embodiments of the invention and that various changes and modifications may be made thereto without departing from the spirit and scope of the invention as defined in the appended claims.

What is claimed is:

1. A cathodoluminescence detector for receiving light emitted from a specimen irradiated by an electron beam, the cathodoluminescence detector comprising:
   a clear hollow tube having first and second end portions;
   a concave mirror mounted at said first end portion for receiving light from the specimen and reflecting the same into said tube;
   a vacuum window mounted at said second end portion;
   said tube defining a longitudinal axis and having a reflective inner wall surface for conducting the light from said concave mirror to said vacuum window; and,
   a photoelectric receiver mounted next to said vacuum window for receiving the light passing through the latter from said tube.

2. The cathodoluminescence detector of claim 1, wherein said concave mirror is a spherical concave mirror.

3. The cathodoluminescence detector of claim 1, wherein said concave mirror is an aspherical concave mirror.

4. The cathodoluminescence detector of claim 1, said vacuum window being disposed at said second end portion so as to extend into said tube.

5. The cathodoluminescence detector of claim 1, said vacuum window being a cylindrically-shaped part which is mounted at said second end portion of said tube so as to extend at least partially into the latter; and, said detector further comprising: a sealing ring disposed between said tube and said vacuum window; and, securing means for pressing said seal in the direction of said longitudinal axis to effect a vacuum-tight connection between said tube and said vacuum window.

6. The cathodoluminescence detector of claim 5, said cylindrically-shaped part being made of glass.

7. The cathodoluminescence detector of claim 5, said cylindrically-shaped part being made of plastic.

8. The cathodoluminescence detector of claim 1, said receiver having a window mounted directly behind said vacuum window.

9. The cathodoluminescence detector of claim 1, said detector further comprising: a housing for accommodating said concave mirror therein; and, interface means for mounting said housing on said tube in a reproducible manner.

10. The cathodoluminescence detector of claim 1, said tube being made of aluminum.

11. The cathodoluminescence detector of claim 1, said concave mirror being made of aluminum.

12. The cathodoluminescence detector of claim 1, said concave mirror having a reflective layer of aluminum formed thereon.

13. The cathodoluminescence detector of claim 1, comprising a filter disposed between said receiver and vacuum window.

14. The cathodoluminescence detector of claim 1, comprising a monochromator disposed between said receiver and said vacuum window.

15. A cathodoluminescence detector arrangement for a scanning electron microscope which generates an electron beam for scanning a specimen, the microscope including a specimen chamber for holding the specimen to be investigated and the chamber having a mounting wall, the arrangement comprising:
a clear hollow tube having first and second end portions;
a concave mirror disposed at said first end portion for receiving light from the specimen and reflecting the same into said tube;
a vacuum window mounted at said second end portion;
said tube defining a longitudinal axis and having a reflective inner wall surface for conducting the light from said concave mirror to said vacuum window;
a photoelectric receiver mounted next to said vacuum window for receiving the light passing through the latter from said tube;
said receiver and said tube being an interconnected assembly mounted on the mounting wall of the specimen chamber so as to be displaceable with respect thereto in the direction of said axis;
sealing means for permitting a seal-tight displacement of said assembly relative to the specimen chamber; and,
said assembly including means for providing a reproducible positioning of said first end portion when said assembly is adjusted to place said concave mirror above the specimen to receive light emanating therefrom.

16. The cathodoluminescence detector of claim 15, said concave mirror being a rotational ellipsoid having a semiaxis quotient of a/b lying in the range of 1.01 to 1.05 wherein (a) is the large semiaxis and (b) is the small semiaxis with said large semiaxis (a) lying in the plane of the specimen and being the rotation axis.

17. The cathodoluminescence detector of claim 15, said concave mirror being a curved surface having first and second ends with respective radii of curvature (a) and (b) at said ends;
said concave surface having an opening of diameter (c) formed therein for passing the electron beam to the specimen;
said first end portion of said tube having an end face disposed in a plane inclined with respect to the vertical at an angle (w) and said tube having an inner diameter (i);
said electron beam defining a beam axis and said end face of said tube being disposed a distance (e) from said beam axis; and,
said tube having a bottom at elevation (d) above the specimen.

18. The cathodoluminescence detector of claim 17, wherein:
a=18.5 mm
b=18.0 mm
c=5 mm
d=0.5 mm
e=3.5 mm
i=14 mm
w=12°.

19. The cathodoluminescence detector of claim 15, comprising mounting means for detachably mounting said concave mirror to said tube to facilitate the mounting and replacement of said concave mirror on said tube.

20. A cathodoluminescence detector arrangement for a scanning electron microscope which generates an electron beam for scanning a specimen, the microscope including a specimen chamber for holding the specimen to be investigated and the chamber having a mounting wall, the arrangement comprising:
a clear hollow tube having first and second end portions;
a concave mirror disposed at said first end portion for receiving light from the specimen and reflecting the same into said tube;
mounting means for detachably mounting said concave mirror to said tube to facilitate the mounting and replacement of said concave mirror on said tube;
a vacuum window mounted at said second end portion;
a photoelectric receiver mounted next to said vacuum window for receiving the light passing through the latter from said tube;
said receiver and said tube being an interconnected assembly mounted on the mounting wall of the specimen chamber so as to be displaceable with respect thereto in the direction of said axis;
sealing means for permitting a seal-tight displacement of said assembly relative to the specimen chamber;
said assembly including means for providing a reproducible positioning of said first end portion when said assembly is adjusted to place said concave mirror above the specimen to receive light emanating therefrom; and,
said mounting means including alignment means for aligning said concave mirror with respect to said tube.

21. A cathodoluminescence detector arrangement for a scanning electron microscope which generates an electron beam for scanning a specimen, the microscope including a specimen chamber for holding the specimen to be investigated and the chamber having a mounting wall, the arrangement comprising:

a clear hollow tube having first and second end portions;

a concave mirror disposed at said first end portion for receiving light from the specimen and reflecting the same into said tube;

mounting means for detachably mounting said concave mirror to said tube to facilitate the mounting and replacement of said concave mirror on said tube;

a vacuum window mounted at said second end portion;

a photoelectric receiver mounted next to said vacuum window for receiving the light passing through the latter from said tube;

said receiver and said tube being an interconnected assembly mounted on the mounting wall of the specimen chamber so as to be displaceable with respect thereto in the direction of said axis;

sealing means for permitting a seal-tight displacement of said assembly relative to the specimen chamber;

said assembly including means for providing a reproducible positioning of said first end portion when said assembly is adjusted to place said concave mirror above the specimen to receive light emanating therefrom;

said concave mirror being disposed at an elevation above the specimen; and, said tube being likewise disposed at an elevation above the specimen and having an opening at said first end portion disposed directly adjacent said concave mirror.

22. A cathodoluminescence detector for receiving light emitted from a specimen irradiated by an electron beam, the cathodoluminescence detector comprising:

a clear hollow tube having first and second end portions;

a concave mirror mounted at said first end portion for receiving light from the specimen and reflecting the same into said tube;

a vacuum window mounted at said second end portion;

said tube defining a longitudinal axis and having a reflective inner wall surface for conducting the light from said concave mirror to said vacuum window;

a photoelectric receiver mounted next to said vacuum window for receiving the light passing through the latter from said tube; and, mounting means for detachably mounting said concave mirror to said tube thereby facilitating the mounting and replacement of said concave mirror on said tube.

23. The cathodoluminescence detector of claim 22, said mounting means including alignment means for aligning said concave mirror with respect to said tube.

24. A cathodoluminescence detector for receiving light emitted from a specimen irradiated by an electron beam, the cathodoluminescence detector comprising:

a clear hollow tube having first and second end portions;

a concave mirror mounted at said first end portion for receiving light from the specimen and reflecting the same into said tube;

a vacuum window mounted at said second end portion;

said tube defining a longitudinal axis and having a reflective inner wall surface for conducting the light from said concave mirror to said vacuum window;

a photoelectric receiver mounted next to said vacuum window for receiving the light passing through the latter from said tube;

said concave mirror being disposed at an elevation above the specimen; and, said tube being likewise disposed at an elevation above the specimen and having an opening at said first end portion disposed directly adjacent said concave mirror.

* * * * *